(12) United States Patent
Catinat et al.

(10) Patent No.: US 6,590,112 B1
(45) Date of Patent: Jul. 8, 2003

(54) METHOD FOR MAKING AN OXIRANE

(75) Inventors: Jean-Pièrre Catinat, Waudrez (BE);
Michel Strebelle, Brussels (BE)

(73) Assignee: Solvay (Société Anonyme), Brussels (BE)

( * ) Notice: Subject to any disclaimer, the term of this patent is extended or adjusted under 35 U.S.C. 154(b) by 0 days.

(21) Appl. No.: 09/850,748

(22) PCT Filed: Nov. 11, 1999

(86) PCT No.: PCT/EP99/08703

§ 371 (c)(1),
(2), (4) Date: Aug. 6, 2001

(87) PCT Pub. No.: WO00/31057

PCT Pub. Date: Jun. 2, 2000

(30) Foreign Application Priority Data

Nov. 20, 1998 (BE) ............................................. 09800840

(51) Int. Cl.⁷ ...................... C07D 301/12; C07D 301/19
(52) U.S. Cl. ........................................ 549/531; 549/529
(58) Field of Search .................................. 549/531, 529

(56) References Cited

U.S. PATENT DOCUMENTS

| 5,374,747 A | 12/1994 | Saxton et al. ................ 549/531 |
| 5,412,122 A | 5/1995 | Saxton et al. ................ 549/531 |
| 5,591,875 A | 1/1997 | Chang et al. ................ 549/531 |

FOREIGN PATENT DOCUMENTS

| EP | 0 230 949 | 8/1987 |
| EP | 0 659 685 | 6/1995 |
| EP | 0 712 852 | 5/1996 |
| WO | WO 98/43736 | 10/1998 |

*Primary Examiner*—Ba K. Trinh
(74) *Attorney, Agent, or Firm*—Oblon, Spivak, McClelland, Maier & Neustadt, P.C.

(57) ABSTRACT

Continuous process for manufacturing an oxirane, according to which an olefin is reacted at a temperature above 35° C. and for a period of more than 48 hours, with a peroxide compound in the presence of a zeolite-based catalyst and in the presence of a metal salt, in which the catalyst undergoes no regeneration treatment and in which the rate of deactivation of the catalyst, expressed as being a percentage of the conversion of the peroxide compound lost per gram of oxirane produced per gram of zeolite determined after establishing the reaction conditions, i.e. after the consumption of 2.5 mol of peroxide function per gram of zeolite, is less than or equal to 0.15%.

9 Claims, 1 Drawing Sheet

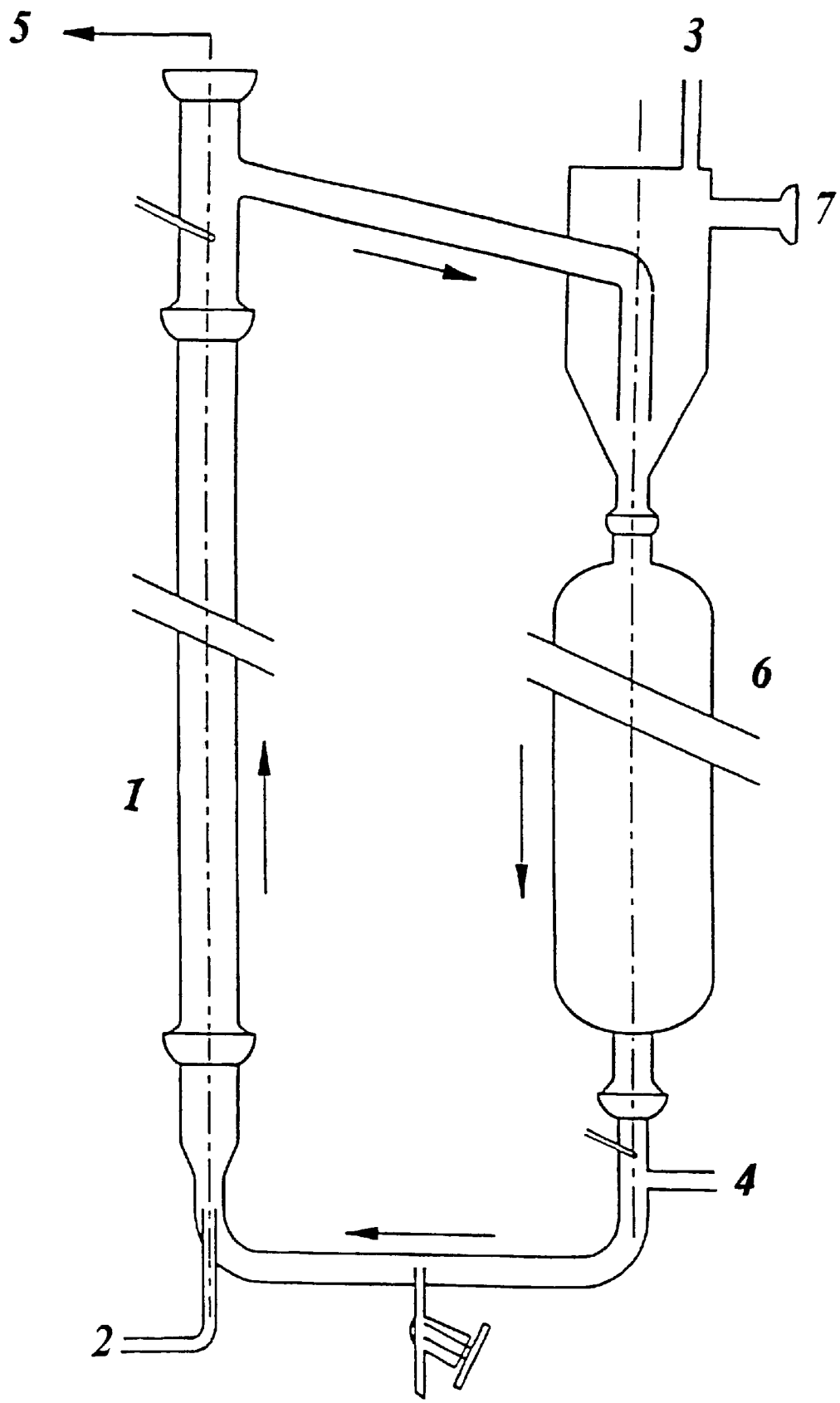

METHOD FOR MAKING AN OXIRANE

This application is a 371 of PCT/EP99/08703 dated Nov. 11, 1999.

The invention relates to a continuous process for the manufacture of an oxirane by reaction between an olefin and a peroxide compound in the presence of a zeolite-based catalyst. The invention relates more particularly to a process for manufacturing 1,2-epoxypropane (or propylene oxide) by reaction between propylene and hydrogen peroxide.

It is known practice to manufacture propylene oxide by epoxidation of propylene using hydrogen peroxide and in the presence of a catalyst of TS-1 type, as described, for example, in patent application EP 0,230,949. This known process has the drawback of leading, under certain conditions, to poor selectivities and a deactivation of the catalyst.

Patent application EP 0,712,852 describes the use of a metal salt for this reaction, but these reaction conditions require a periodic or very frequent regeneration of the catalyst.

The invention is directed towards overcoming this drawback by providing a continuous process for manufacturing an oxirane, which exhibits high selectivity while at the same time producing only minimal deactivation of the catalyst.

The invention consequently relates to a continuous process for manufacturing an oxirane by reaction, at a temperature above 35° C. and for a period of more than 48 hours, of an olefin with a peroxide compound in the presence of a zeolite-based catalyst and in the presence of a salt, in which the catalyst undergoes no regeneration treatment and in which the rate of deactivation of the catalyst, expressed as being a percentage of the conversion of the peroxide compound lost per gram of oxirane produced per gram of zeolite determined after establishing the reaction conditions, i.e. after the consumption of 2.5 mol of peroxide function per gram of zeolite, remains less than or equal to 0.15%.

One of the essential features of the invention lies in the addition of a salt. The reason for this is that it has been found that the presence of a salt in the epoxidation reaction medium limits the side reactions which give rise to the formation of unwanted by-products. The addition of a salt thus makes it possible to increase the selectivity.

Another particular feature of the invention lies in a minimal deactivation of the catalyst after establishing the reaction conditions, i.e. after the consumption of 2.5 mol of peroxide (—OOH) function per gram of zeolite. More particularly, the rate of deactivation of the catalyst is expressed as being a percentage of conversion of the peroxide compound lost per gram of oxirane produced per gram of zeolite determined after establishing the reaction conditions, i.e. after the consumption of 2.5 mol of peroxide function per gram of zeolite. The rate of deactivation of the catalyst is less than or equal to 0.15%. Advantageously, this rate of deactivation is less than or equal to 0.1%. The rate of deactivation is preferably less than or equal to 0.05%.

Yet another essential feature of the process of the invention lies in the temperature at which the olefin reacts with the peroxide compound in the presence of the catalyst and the metal salt. The reason for this is that the Applicant has found that a temperature above 35° C. makes it possible to overcome the gradual deactivation of the catalyst and that the presence of a metal salt makes it possible to carry out the reaction at a substantially higher temperature without, however, any appreciable reduction in the reaction selectivity being observed. It is advantageous to carry out the reaction at a temperature above or equal to 40° C. and preferably above or equal to 45° C. A temperature above or equal to 50° C. is most particularly preferred. However, the reaction temperature is generally below 100° C. and preferably below 80° C.

The salt used in the process according to the invention can be a metal salt or an ammonium salt. Generally, the metal is chosen from alkali metals and alkaline-earth metals. The alkali metals most usually used are lithium, sodium, potassium and caesium. The alkaline-earth metals which can be used in the context of the present invention are mainly magnesium, calcium, strontium and barium.

The metal salts used are mainly halides, oxides, hydroxides, carbonates, sulphates, phosphates and organic acid salts such as acetates. The halides are generally fluorides, chlorides, bromides and iodides. A preference is shown for chlorides.

The salt used in the process according to the present invention is preferably an alkali metal halide and advantageously sodium chloride.

The amount of metal salt used in the present process is expressed as the content of ammonium or metal ions from the salt relative to the amount of catalyst expressed in millimol (mmol) of metal or of ammonium per gram of zeolite. Generally, the salt is introduced such that its content in the reaction medium is greater than or equal to $10^{-4}$ mmol/g of zeolite and less than or equal to 10 mmol/g of zeolite. Advantageously, the metal salt content is greater than or equal to $10^{-3}$ mmol/g of zeolite and less than or equal to 1 mmol/g of zeolite. A preference is shown for a content of greater than or equal to $10^{-2}$ mmol/g of zeolite and less than or equal to 0.5 mmol/g of zeolite.

The catalysts used in the process according to the invention contain a zeolite, i.e. a solid containing silica which has a microporous crystalline structure. The zeolite is advantageously free of aluminium. It preferably contains titanium.

The zeolite which can be used in the process according to the invention can have a crystal structure of ZSM-5, ZSM-11 or MCM-41 type or of beta-zeolite type. Zeolites of ZSM-5 type are suitable for use. Those with an infrared adsorption band at about 950–960 cm$^{-1}$ are preferred.

The zeolites which are particularly suitable are titanium silicalites. Those corresponding to the formula $xTiO_2(1-x)SiO_2$ in which x is from 0.0001 to 0.5, preferably from 0.001 to 0.05, give high-quality performance. Materials of this type, known under the name TS-1 and having a crystal structure of ZSM-5 type, give particularly favourable results.

Advantageously, the catalyst is in the form of spherical particles obtained by dispersing a sol containing zeolite crystals with a compound capable of forming a gel in the zone of a reactor containing a reaction gas such that the sol becomes fragmented into grains of sol at the reaction zone inlet. The grains of sol flow in the reaction zone along a curvilinear trajectory and, in doing so, the grains of sol solidify to a gel and can be collected.

The catalyst particles generally have an average diameter of greater than or equal to 0.01 mm and less than or equal to 5 mm, a specific surface of greater than or equal to 1 m$^2$/g and less than or equal to 900 m$^2$/g (determined according to the nitrogen adsorption method), an apparent density of between 0.1 and 1.0 g/ml, a pore volume of between 0.25 and 2.5 ml/g and a pore diameter distribution with a maximum of between 15 and 2000 Å.

In one particular embodiment of the process according to the invention, the reaction is carried out continuously in a reactor in the liquid phase in the presence of a solvent, and a gaseous compound is introduced continuously into the reactor at a flow rate which is sufficient to entrain some of the oxirane produced, which is collected with the gaseous compound at the place at which this gaseous compound leaves the reactor. This specific embodiment can be advantageous since it has been observed that the oxirane reacts in the epoxidation reaction medium with the water which accompanies the peroxide compound and/or the solvent to form by-products, thereby reducing the selectivity of the epoxidation reaction. By introducing a gaseous compound into the reaction medium at a flow rate which is sufficient to entrain the oxirane produced and remove it from the reactor at the same time as the gaseous compound, the contact time between the oxirane produced and the epoxidation reaction medium is reduced. This thus avoids the formation of by-products and increases the selectivity of the epoxidation.

The function of the gaseous compound is to entrain the oxirane produced out of the reaction medium in order to prevent the oxirane from remaining in contact with the reaction medium for too long and thus to prevent the formation of side by-products. In other words, the gaseous compound makes it possible to remove the oxirane produced from the reaction medium by stripping.

The gaseous compound used in the specific embodiment of the process according to the invention can be any compound which is in gaseous form under the epoxidation conditions and which has no negative influence on the epoxidation reaction. It can be chosen from inert gases such as nitrogen.

Generally, in the specific embodiment of the process according to the invention, the olefin is introduced into the reactor in gaseous form and in a large excess such that the gaseous olefin can act, partially or completely, as the gaseous compound, i.e. such that it can entrain the oxirane produced and remove it from the reactor.

Advantageously, the gaseous compound is introduced into the reactor at a flow rate such that it makes it possible not only to entrain at least some of the oxirane produced but also to circulate the liquid phase in the reactor, in particular when this reactor is of loop type.

Generally, the gaseous compound is introduced into the reactor at a flow rate such that the ratio of the molar flow rate of the gaseous compound to the molar feed flow rate of the peroxide compound is at least 5, in particular at least 8, values of at least being common. The ratio of these molar flow rates is generally less than or equal to 50, in particular less than or equal to 30, values less than or equal to 20 being common.

Any type of reactor can be used in the process according to the invention, in particular a reactor of loop type. A fixed-bed reactor may also be suitable. Reactors of bubble-siphon loop type, in which the circulation of the liquid and optionally also of the catalyst is obtained by bubbling a gas into one of the arms, is particularly suitable. An example of such a reactor is represented schematically in FIG. 1. The gaseous compound (preferably the olefin) is introduced into the bottom of the reaction zone 1 via the pipe 2. The other reagents (peroxide compound, solvent, catalyst, one or more optional additives) are introduced into the reactor via the pipes 3 and 4. The liquid phase circulates in the reactor in the direction of the arrows. The gaseous compound rises in the reaction zone 1 and thus entrains the oxirane produced therein. A mixture of the gaseous compound and oxirane produced leaves the reactor via the pipe 5. The liquid phase leaving from the top of the reaction zone 1 is recycled into the bottom of the reaction zone via a heat exchanger 6. The liquid phase, which is depleted in oxirane by virtue of stripping, overflows via the pipework 7. A reactor comprising 2 concentric zones can also be used in the process according to the invention, the central zone providing the function of zone 1 of the reactor represented schematically in FIG. 1, and. the peripheral zone providing the function of the zone 6 of the reactor represented schematically in FIG. 1.

In the process according to the invention, it may moreover prove advantageous to maintain the pH of the liquid phase during the reaction between the olefin and the peroxide compound at a value of at least 4.8, in particular at least 5. The pH is advantageously less than or equal to 6.5, in particular less than or equal to 6. Good results are obtained when the pH is from 4.8 to 6.5, preferably from 5 to 6. The pH of the liquid phase during the epoxidation reaction can be controlled by adding a base. This base can be chosen from water-soluble bases. They may be strong bases. They may also be weak bases.

The peroxide compounds which can be used in the process according to the invention are peroxide compounds containing one or more peroxide (—OOH) functions which can release active oxygen and which are capable of carrying out an epoxidation. Hydrogen peroxide and peroxide compounds which can produce hydrogen peroxide under the epoxidation reaction conditions are suitable for use. Hydrogen peroxide is preferred.

Generally, the molar ratio between the amount of olefin used and the amount of peroxide compound used is greater than or equal to 0.1 and less than or equal to 100. Advantageously, this ratio is greater than or equal to 1 and less than or equal to 50. Preferably, this ratio is greater than or equal to 5 and less than or equal to 25.

In the process according to the invention, when it is carried out continuously, the peroxide compound is generally used in an amount of at least 0.005 mol per hour and per gram of zeolite, in particular at least 0.01 mol per hour and per gram of zeolite. The amount of peroxide compound is usually less than or equal to 2.5 mol per hour and per gram of zeolite and in particular less than or equal to 1 mol per hour and per gram of zeolite. A preference is shown for an amount of peroxide compound of greater than or equal to 0.03 mol per hour and per gram of zeolite and less than or equal to 0.25 mol per hour and per gram of zeolite.

In the process according to the invention, the peroxide compound is advantageously used in the form of an aqueous solution. In general, the aqueous solution contains at least 10% by weight of peroxide compound, in particular at least 20% by weight. It usually contains not more 70% by weight of peroxide compound, in particular 50% by weight.

The oxirane which can be prepared by the process according to the invention is an organic compound comprising a group corresponding to the general formula:

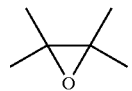

The oxirane generally contains from 2 to 20 carbon atoms, preferably from 3 to 10 carbon atoms. An oxirane which can advantageously be prepared by the process according to the invention is 1,2-epoxypropane.

Olefins which are suitable in the process according to the invention generally contain from 2 to 20 carbon atoms and preferably from 3 to 10 carbon atoms. Propylene is preferred.

The solvents which can be used in the process according to the invention may be aliphatic organic derivatives containing from 1 to 4 carbon atoms. Methanol may be mentioned by way of example.

EXAMPLES 1 AND 2
(In Accordance with the Invention)

Propylene oxide was manufactured in a bubble-siphon reactor as represented schematically in FIG. 1, by reaction between propylene and 35% hydrogen peroxide in the presence of methanol and catalyst TS-1, used in the form of beads 0.5 mm in diameter.

The tests were carried out at a temperature of 56° C., with a continuous feed of hydrogen peroxide at a flow rate of 0.17 mol/h. The amount of methanol present in the reactor was 16 mol/mol of $H_2O_2$. 75 Nl/h of propylene (i.e. 3.3 mol/h) were injected. At this flow rate, the introduction of propylene into the reactor brought about circulation of the liquid reaction medium and of the catalyst in suspension. The amount of propylene used was 19.6 mol/mol of $H_2O_2$. The volume of liquid in the reactor was 207 ml.

In Example 1, 1.58 g of TS-1 were introduced and sodium chloride was added in an amount such that the sodium content in the reaction medium was 0.1 mmol of sodium per gram of catalyst.

A selectivity towards propylene oxide of 96.7% was obtained and the degree of conversion of the $H_2O_2$ fell from 35.2% after 25 hours (the amount of $H_2O_2$ used per gram of TS-1 is 2.7 mol) to 31.1% after 140 hours (the amount of $H_2O_2$ used per gram of TS-1 is 15.2 mol). The rate of deactivation, expressed as a percentage, is 0.048%.

In Example 2, 4.73 g of TS-1 were introduced and sodium chloride was added in an amount such that the sodium chloride in the reaction medium was 0.08 mmol of sodium per gram of TS-1. A selectivity towards propylene oxide of 96.2% was obtained and the degree of conversion of the $H_2O_2$ fell from 53.1% after 75 hours (the amount of $H_2O_2$ used per gram of TS-1 is 2.7 mol) to 45.0% after 420 hours (the amount of $H_2O_2$ used per gram of TS-1 is 15.2 mol). The rate of deactivation is 0.035%.

The selectivity towards propylene oxide is given by the molar ratio, expressed as a percentage, between the amount of propylene oxide obtained divided by the sum of all the organic products formed).

EXAMPLE 3
(Comparative)

Example 1 is repeated, but at 35° C. and without adding sodium chloride. In this case, a selectivity of 93.1% was obtained and the degree of conversion of the $H_2O_2$ fell from 35.9% after 25 hours (the amount of $H_2O_2$ used per gram of TS-1 is 2.7 mol) to 22.4% after 140 hours (the amount of $H_2O_2$ used per gram of TS-1 is 15.2 mol), i.e. a markedly faster decrease than in Example 1. The rate of deactivation is 0.15%.

What is claimed is:

1. Continuous process for manufacturing an oxirane by continuous reaction in a reactor in the liquid phase in the presence of a solvent, at a temperature above 35° C. and for a period of more than 48 hours, of an olefin with a peroxide compound in the presence of a zeolite-based catalyst and in the presence of a salt, in which the catalyst undergoes no regeneration treatment, the rate of deactivation of the catalyst, expressed as being a percentage of the conversion of the peroxide compound lost per gram of oxirane produced per gram of zeolite determined-after establishing the reaction conditions, i.e. after the consumption of 2.5 mol of peroxide function per gram of catalyst, remains less than or equal to 0.15%, and in that a gaseous compound is introduced continuously into the reactor at a flow rate which is sufficient to entrain some of the oxirane produced, which is collected with gaseous compound at the place at which this gaseous compound leaves the reactor.

2. Process according to claim 1, in which the salt is a metal salt, preferably an alkali metal halide or an ammonium salt.

3. Process according to claim 1, in which the content of metal ions from the metal salt relative to the amount of catalyst, expressed in millimoles of metal per gram of zeolite, is greater than or equal to $10^{-4}$ mmol/g of zeolite and less than or equal to 10 mmol/g of zeolite.

4. Process according to claim 1, in which the temperature at which the olefin reacts with the peroxide compound in the presence of the catalyst and the metal salt is below 100° C., and advantageously above 50° C. and below 80° C.

5. Process according to claim 1, in which the catalyst is titanium silicalite, preferably of TS-1 type with a crystal structure of ZSM-5 type.

6. Process according to claim 1, in which the reactor is of the bubble-siphon loop type in which the flow rate of the gaseous compound is sufficient to circulate the liquid phase in the loop reactor and in which the ratio of the molar flow rate of the gaseous compound to the molar feed flow rate of the peroxide compound is greater than or equal to 5, preferably greater than or equal to 10.

7. Process according to claim 1, in which the peroxide compound is used in an amount of from 0.005 to 2.5 mol per hour and per gram of zeolite, preferably from 0.03 to 0.25 mol per hour and per gram of zeolite, and in which the peroxide compound is used in the form of an aqueous solution containing from 10 to 70% of peroxide compound, preferably from 20 to 50%.

8. Process according to claim 1, in which the pH of the liquid phase is maintained at from 4.8 to 6.5 by adding a base to the liquid phase.

9. Process according to claim 1, in which the oxirane is 1,2-epoxypropane, the olefin is propylene and the peroxide compound is hydrogen peroxide.

* * * * *